(12) United States Patent
Berndt (10) Patent No.: US 8,942,790 B2
(45) Date of Patent: *Jan. 27, 2015

(54) NEEDLE AND RELATED METHODS

(71) Applicant: Boston Scientific Scimed, Inc., Maple Grove, MN (US)

(72) Inventor: Malka S. Berndt, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/155,516

(22) Filed: Jan. 15, 2014

(65) Prior Publication Data

US 2014/0135630 A1    May 15, 2014

Related U.S. Application Data

(63) Continuation of application No. 11/825,929, filed on Jul. 10, 2007, now Pat. No. 8,666,479.

(60) Provisional application No. 60/819,586, filed on Jul. 10, 2006.

(51) Int. Cl.
*A61B 5/00* (2006.01)
*A61M 5/158* (2006.01)
*A61B 17/34* (2006.01)
*A61B 17/00* (2006.01)
(Continued)

(52) U.S. Cl.
CPC ............. *A61B 5/0075* (2013.01); *A61B 5/0084* (2013.01); *A61M 5/158* (2013.01); *A61B 17/3478* (2013.01); *A61B 2017/00048* (2013.01);
(Continued)

(58) Field of Classification Search
None
See application file for complete search history.

(56) References Cited

U.S. PATENT DOCUMENTS 3,941,121 A    3/1976    Olinger et al.
4,668,226 A    5/1987    Omata et al.
(Continued)

FOREIGN PATENT DOCUMENTS

WO    WO 92/14399 A1    9/1992
WO    WO 02/30304 A1    4/2002

*Primary Examiner* — Parikha Mehta
(74) *Attorney, Agent, or Firm* — Bookoff McAndrews, PLLC (57) ABSTRACT

An optical spectroscopic injection needle assembly. According to one embodiment, the assembly may include an injection needle, a light source, a spectrometer, a computer and an indicator. The injection needle, in turn, may include a hollow outer needle, a hollow inner needle, a pair of optical fibers, an inner catheter, an outer catheter, an inner hub and an outer hub. The proximal end of the outer needle may be fixedly mounted within the distal end of the inner catheter. The distal end of the inner hub may be fixedly mounted on the proximal end of the inner catheter, the proximal end of the inner hub being suited for connection to a syringe. The inner needle, as well as the distal ends of the optical fibers, may be positioned within the outer needle and may be held in place by an optical bonding material. The proximal ends of the optical fibers may extend from a side arm of the inner hub, one fiber may be coupled to the light source, the other fiber may be coupled to the spectrometer. The inner catheter and the outer needle may be slidably mounted within the outer catheter to permit the outer needle to be selectively extended or retracted from the distal end of the outer catheter. The outer hub may be fixedly mounted on the proximal end of the outer catheter. In use, as the outer needle may be inserted into a tissue, the tissue may be illuminated and the reflected light may be detected and compared to standards for various tissue types. The results of the comparison may then be indicated.

20 Claims, 6 Drawing Sheets

(51) Int. Cl.
  *A61B 19/00* (2006.01)
  *A61M 25/00* (2006.01)

(52) U.S. Cl.
  CPC .......... *A61B 2017/00061* (2013.01); *A61B 2019/5231* (2013.01); *A61M 25/0084* (2013.01)
  USPC .................................................. 600/476

(56) References Cited

U.S. PATENT DOCUMENTS

| | | |
|---|---|---|
| 4,946,442 A | 8/1990 | Sanagi |
| 5,210,814 A | 5/1993 | McNally |
| 5,718,702 A | 2/1998 | Edwards |
| 5,785,689 A | 7/1998 | de Toledo et al. |
| 5,991,653 A | 11/1999 | Richards-Kortum et al. |
| 6,238,335 B1 | 5/2001 | Silverman et al. |
| 6,251,063 B1 | 6/2001 | Silverman et al. |
| 6,336,915 B1 | 1/2002 | Scarfone et al. |
| 6,351,064 B1 | 2/2002 | Frayssinet |
| 6,401,718 B1 | 6/2002 | Johnson et al. |
| 6,423,034 B2 | 7/2002 | Scarfone et al. |
| 6,585,694 B1 | 7/2003 | Smith et al. |
| 6,695,764 B2 | 2/2004 | Silverman et al. |
| 6,770,053 B2 | 8/2004 | Scarfone et al. |
| 2004/0158136 A1 | 8/2004 | Gough et al. |

NEEDLE AND RELATED METHODS

CROSS-REFERENCE TO RELATED APPLICATIONS

The present application is a Continuation Application of U.S. patent application Ser. No. 11/825,929, filed Jul. 10, 2007, now U.S. Pat. No. 8,666,479, which is a non-provisional Patent Application of and claims the benefit under 35 U.S.C. 119(e) of U.S. Provisional Patent Application Ser. No. 60/819,586, filed Jul. 10, 2006, all of which are incorporated herein by reference.

BACKGROUND OF THE INVENTION

The present invention relates generally to injection needles and relates more particularly to an injection needle incorporating visualization.

Nearly half of all Americans suffer from heartburn at least once a month. Heartburn occurs when stomach fluids and acids escape from the stomach and enter into the esophagus, irritating the esophagus. Normally, a muscular ring called the lower esophageal sphincter (LES) acts as a valve between the esophagus and the stomach to allow food to pass from the esophagus into the stomach while keeping stomach fluids and acids from escaping from the stomach into the esophagus. In those instances in which the LES fails to keep stomach fluids and acids in the stomach, heartburn occurs.

For some people who suffer from heartburn, the heartburn is severe enough or frequent enough to disrupt their daily activities and/or their sleep. Such a condition is called gastroesophageal reflux disease (GERD). In some people who have GERD, the LES relaxes more than it should and/or at the wrong times.

In addition to causing frequent and/or severe heartburn, GERD can cause other health problems. For example, the fluids and acids that reflux into the esophagus can lead to inflammation of the esophagus (esophagitis) or ulcers. In severe cases, this damage can scar the esophageal lining and narrow it, causing a stricture which may make it hard or painful for the patient to swallow. In certain cases, this may lead to a condition called Barrett's esophagus, where the lining of the esophagus changes and may over time lead to cancer of the esophagus.

Many people can get relief from GERD symptoms by changing their diet and/or using appropriate medications. Some of the medications available for managing GERD symptoms include common antacids as well as drugs that slow down the production of stomach acids, such as proton pump inhibitors and $H_2$ receptor antagonists.

It should be noted, however, that medications of the type described above merely address symptoms of GERD and do not address the condition's mechanical etiology. Thus, GERD symptoms often recur after drug withdrawal. In addition, while medications may effectively treat the acid-induced symptoms of GERD, they do not treat alkaline reflux, which may result in esophageal mucosal injury.

In any event, because GERD is a chronic condition, it may be necessary for a patient to take medications for the rest of his life in order to continue to obtain relief from GERD symptoms. However, for many patients, the expense and the psychological burden of a lifetime of medication dependence, as well as the uncertainty of long-term effects of some newer medications and the potential for persistent mucosal changes despite symptomatic control, make surgical treatment an alluring alternative to a medicinal approach. As can readily be appreciated, however, surgical intervention, often in the form of anti-reflux surgery, is a major undertaking and includes its own set of risks.

Fortunately, a minimally invasive technique has been devised for treating GERD. This technique, which is more fully disclosed in U.S. Pat. Nos. 6,238,335, 6,251,063, 6,351,064 and 6,695,764, all of which are incorporated herein by reference, typically involves first inserting an endoscope down through the patient's mouth and into the esophagus in proximity to the LES. Then, the distal end of a device commonly referred to as "an injection needle" is inserted through a working channel of the endoscope, and a needle at the distal end of the injection needle is inserted into the muscle of the LES. Then, a special solution is dispensed through the injection needle and into the muscle of the LES. The solution includes a biocompatible polymer that forms a soft, spongy, permanent implant in the sphincter muscle that helps the LES to keep stomach fluids and acids from backing up into the esophagus.

Typically, an injection needle of the type referred to above comprises a hollow needle, a flexible inner catheter, a flexible outer catheter, an inner hub and an outer hub. The proximal end of the hollow needle is typically fixedly mounted within the distal end of the flexible inner catheter. The inner hub is typically fixedly mounted on the proximal end of the inner catheter and is adapted to convey fluids to the inner catheter from a needleless syringe or the like. The inner catheter and the hollow needle are typically slidably mounted within the outer catheter so that one may extend the hollow needle out of the distal end of the outer catheter when one wishes to make an injection and retract the hollow needle into the outer catheter when not making an injection. The outer hub is typically fixedly mounted on the proximal end of the outer catheter and is adapted to engage the inner hub so as to limit the distal movement of the needle and the inner catheter relative to the outer catheter. Examples of injection needles are disclosed in the following patents, all of which are incorporated herein by reference: U.S. Pat. No. 6,770,053; U.S. Pat. No. 6,585,694; U.S. Pat. No. 6,423,034; U.S. Pat. No. 6,401,718; U.S. Pat. No. 6,336,915; U.S. Pat. No. 5,785,689; U.S. Pat. No. 4,946,442; and U.S. Pat. No. 4,668,226.

Typically, certain measures are taken to promote proper placement of the distal tip of the injection needle in the targeted tissue. For example, where the injection needle is delivered to the patient via the working channel of an endoscope, the endoscope is typically additionally equipped with a light and a camera so that one can view, in real-time, the environs of the distal end of the endoscope; in this manner, the targeted penetration site may be identified. In addition, to promote a proper penetration depth of the needle into the targeted tissue, the needle is typically dimensioned to extend from the distal end of the inner catheter by a length corresponding to the desired penetration depth. However, as can be appreciated, tissue thicknesses vary from patient to patient. Moreover, because tissue is easily compressed and because tissue may be penetrated by the inner catheter as well as by the needle, the depth of needle penetration cannot always be controlled by dimensioning the needle in the above manner. For this reason, fluoroscopy is often employed to provide live X-ray images of the injected solution that indicate if the needle has been inserted too far through the tissue.

In addition to being used in the above fashion to treat GERD, injection needles are also useful in injecting other treatment materials, such as drugs, treatments for bleeding, etc.

SUMMARY OF THE INVENTION

According to one aspect of the invention, there is provided an injection needle that may comprise (a) a first catheter, said first catheter comprising a proximal end, a distal end and a longitudinal bore; (b) a first hollow needle, said first hollow needle being designed to extend distally from said distal end of said first catheter, said first hollow needle comprising a distal end adapted for insertion into an object; (c) a tubular member, said tubular member comprising a longitudinal bore, said tubular member being disposed within said first hollow needle, said longitudinal bore of said tubular member being in fluid communication with said longitudinal bore of said first catheter; and (d) fiber optics which may be located within said first hollow needle for transmitting light to an object and for collecting light reflected from the object.

In another embodiment of the invention, an optical spectroscopic injection needle assembly may comprise (a) an injection needle, which may comprise (i) a first catheter, said first catheter having a proximal end, a distal end and a longitudinal bore; (ii) a first hollow needle, said first hollow needle designed to extend distally from said distal end of said first catheter, said first hollow needle comprising a distal end adapted for insertion into an object; (iii) a tubular member, said tubular member comprising a longitudinal bore, said tubular member being disposed within said first hollow needle, said longitudinal bore of said tubular member being in fluid communication with said longitudinal bore of said first catheter; and (iv) fiber optics which may be located within said first hollow needle, in one embodiment, for transmitting light to an object and for collecting light reflected from the object; (b) means, optically coupled to the fiber optics, and adapted to serially illuminate an object at a plurality of wavelengths; (c) means, optically coupled to the fiber optics, provided to detect the light reflected from the illuminated object at said plurality of wavelengths; (d) means for comparing the detected light to appropriate standards; and (e) means for indicating the results of said comparison.

In another embodiment of the invention, a method of treating a tissue may comprise the steps of (a) providing the aforementioned optical spectroscopic injection needle assembly; (b) inserting the first hollow needle into an insertion site of a body part to a first depth; (c) illuminating the body part at said first depth, in one embodiment, using light transmitted through said fiber optics from said serially illuminating means; (d) detecting the light reflected from the illuminated object at said first depth using said detecting means; (e) comparing the detected light to appropriate standards; (f) indicating the results of said comparison; (g) if needed, repeating steps (b) through (f) for other depths or other insertions sites until a desired tissue is located; and (h) injecting a material through the tubular member and into the desired tissue.

For purposes of the present specification and claims, various relational terms like top, bottom, proximal, distal, upper, lower, front, and rear are used to describe the present invention when said invention is positioned in or viewed from a given orientation. It is to be understood that, by altering the orientation of the invention, certain relational terms may need to be adjusted accordingly.

Various objects, features and advantages of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

Referring now to FIGS. 1 through 5, there are shown various views of one embodiment of an optical spectroscopic injection needle assembly constructed according to the teachings of the present invention, said optical spectroscopic injection needle assembly being represented generally by reference numeral 11.

Figure 1:
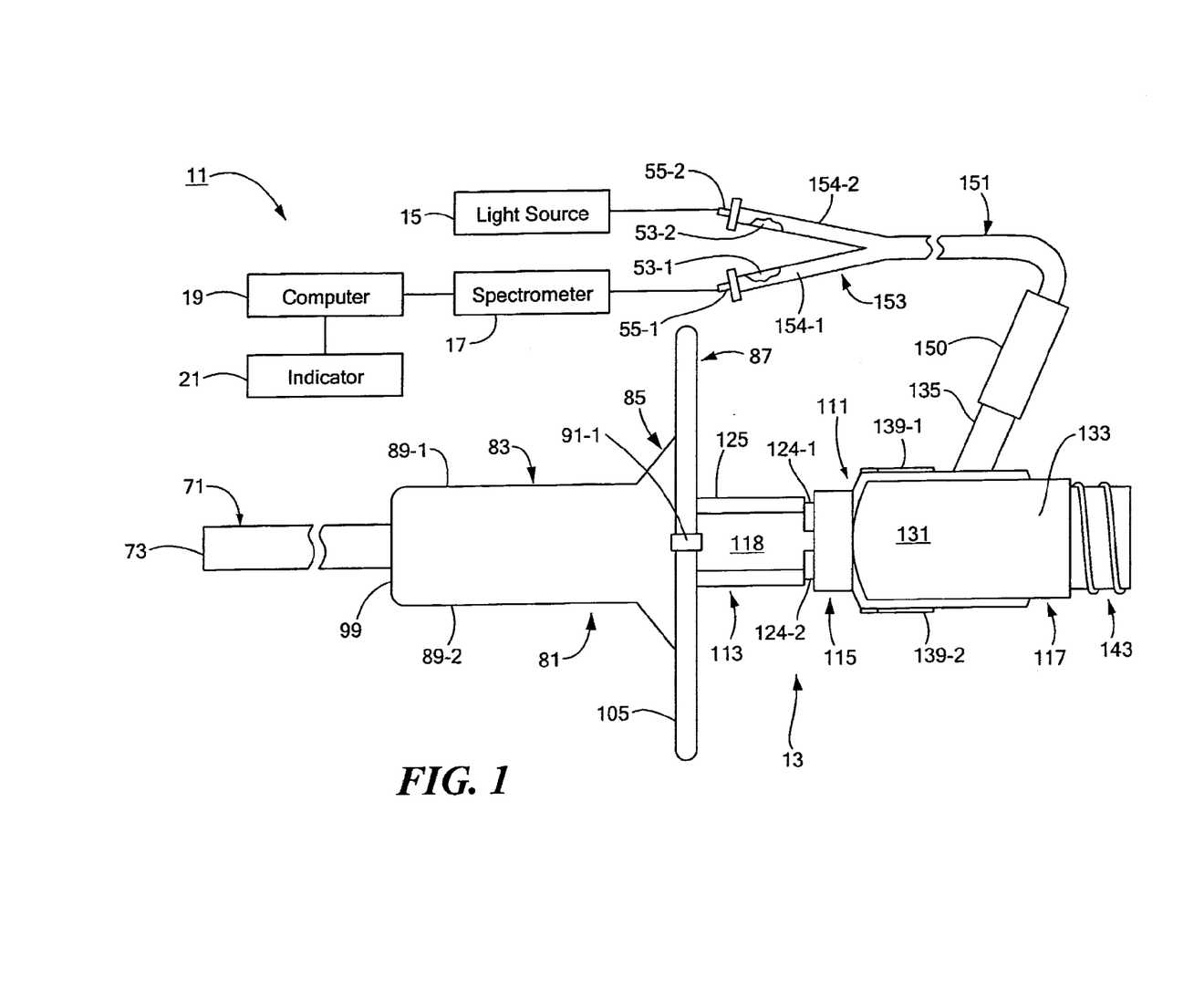
FIG. 1 illustrates a partly schematic side view, broken away in part, of one embodiment of an optical spectroscopic injection needle assembly constructed according to the teachings of the present invention, the assembly being shown with its needle in a retracted position.

Assembly 11 may include an injection needle 13, a light source 15, a spectrometer 17, a computer 19 and an indicator 21.

Figure 3:
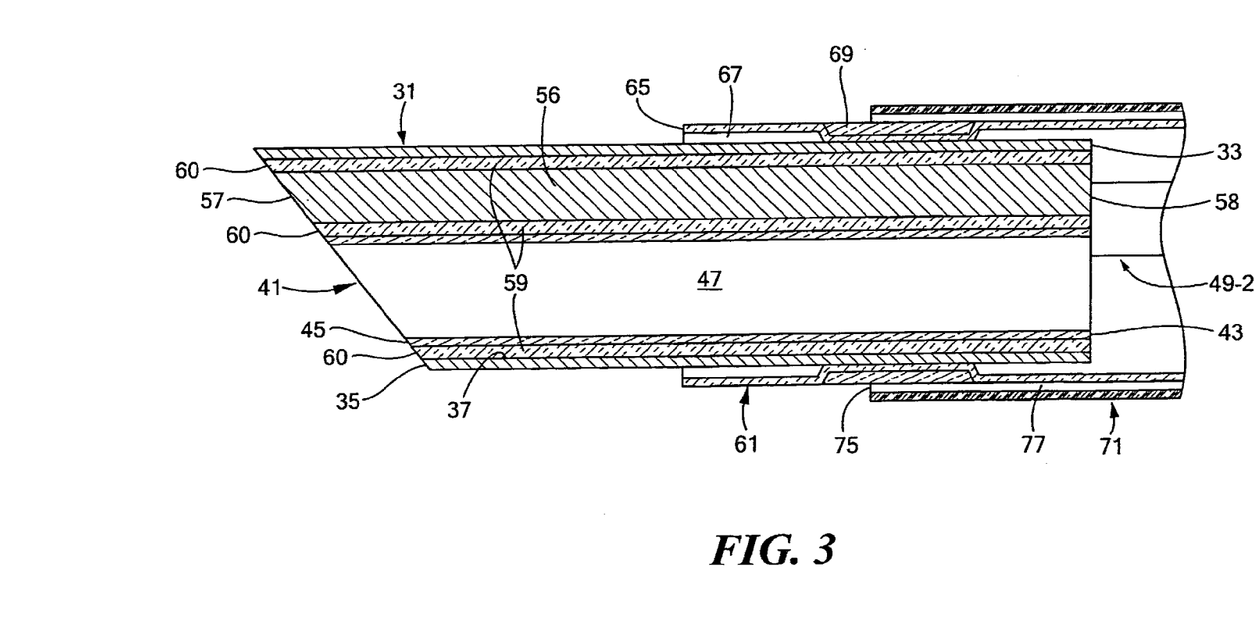
FIG. 3 illustrates an enlarged fragmentary longitudinal section view of the distal end of the optical spectroscopic injection needle assembly of FIG. 1, the assembly being shown with a needle in an extended position.

Injection needle 13 may comprise a hollow outer needle 31. Outer needle 31 may include an elongated, unitary, tubular member of uniform diameter, made of stainless steel or the like, outer needle 13 may be shaped to include a blunt proximal end 33, a beveled distal end 35 and a longitudinal bore 37. Outer needle 31 may be dimensioned to be, for example, a 22 gauge extra thin walled hypodermic needle having a bevel of 18 degrees.

Injection needle 13 may also comprise a hollow inner needle 41. Inner needle 41 may be positioned within bore 37 of outer needle 31. Inner needle 41 may be an elongated, unitary, tubular member of uniform diameter, made of stainless steel or the like. Inner needle 41 may be shaped to include a blunt proximal end 43, a beveled distal end 45 and a longitudinal bore 47. Inner needle 41 may be dimensioned to be, for example, a 25 gauge extra thin walled hypodermic needle having a bevel of 18 degrees. Inner needle 41 may be dimensioned so that blunt proximal end 43 and beveled distal end 45 lie flush with blunt proximal end 33 and beveled distal end 35, respectively, of needle 31. As will be discussed further below, longitudinal bore 47 of inner needle 41 may be used to convey fluids, such as a solution of implant material where injection needle 13 is used to inject such a solution into the LES muscle of a GERD patient. (Alternatively, injection needle 13 may be used to inject therapeutic and diagnostic agents.)

Figure 5:
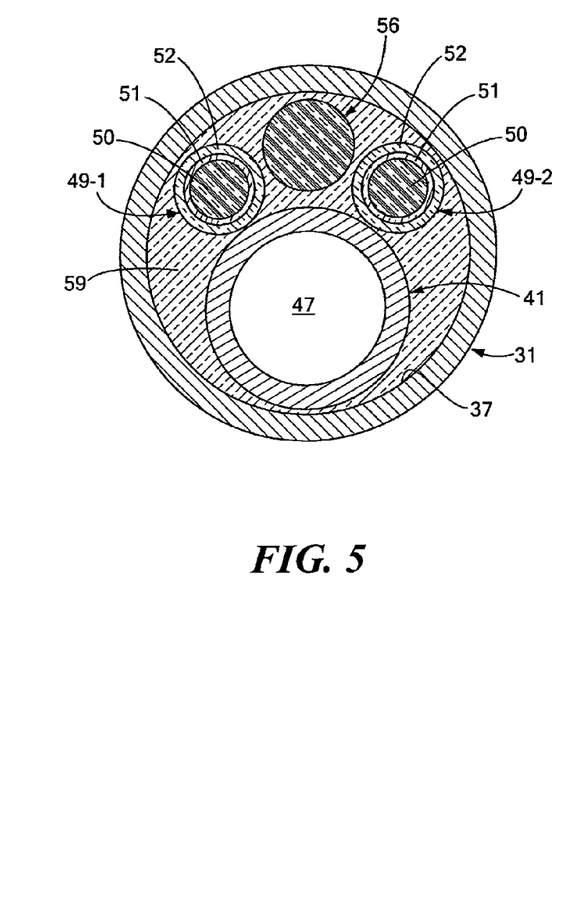
FIG. 5 illustrates an enlarged section view taken along line 1-1 of FIG. 2.

Injection needle 13 may further comprise a pair of optical fibers 49-1 and 49-2, the distal ends (not shown) of optical fibers 49-1 and 49-2 may be inserted into longitudinal bore 37 of needle 31. In the present embodiment, fibers 49-1 and 49-2 may be identical to one another and may be 0.22 NA, step index multimode fibers optimized for the VIS-NIR range, each of fibers 49-1 and 49-2 may include a silica-based core 50 of 100 micron diameter, a silica-based cladding 51 of 110 micron diameter, and a polyimide buffer 52 of 125 micron diameter. The distal ends (not shown) of fibers 49-1 and 49-2 may be beveled and lie flush with distal end 35 of needle 31. The proximal ends 53-1 and 53-2 of fibers 49-1 and 49-2, respectively, may extend proximally beyond proximal end 33 of needle 31 and may be coupled to connectors 55-1 and 55-2, respectively. Examples of connectors suitable for use as connectors 55-1 and 55-2 include SMA 905 connectors.

Injection needle 13 may further comprise a spacer 56, spacer 56 being positioned within bore 37 of outer needle 31. Spacer 56, which may be made of a suitable medical grade plastic or the like, may include an elongated, unitary, solid member that is appropriately dimensioned to keep fibers 49-1 and 49-2 spaced apart at a desired distance. Spacer 56 has a distal end 57 and a proximal end 58. Preferably, distal end 57 is beveled and lies flush with beveled distal end 35 of needle 31. In the present embodiment, proximal end 58 is blunt and lies flush with blunt proximal end 33 of needle 31; however, it should be understood that proximal end 58, if flexible, could extend proximally beyond blunt proximal end 33 of needle 31.

Injection needle 13 may further comprise a bonding material 59, which may comprise an optical bonding material, such as an optical epoxy or like material. Optical bonding material 59 is provided to fill the remaining spaces within bore 37 of outer needle 31 and to bond together the various components positioned within bore 37. The distal end 60 of optical bonding material 59 is shaped to lie flush with beveled distal end 35 of needle 31.

Injection needle 13 further comprises an inner catheter 61. In the present embodiment, inner catheter 61 may include an elongated, unitary, flexible member, for example, made of a suitable medical grade plastic, inner catheter 61 being shaped to include a proximal end 63, a distal end 65 and a longitudinal bore 67. Proximal end 33 of needle 31 may be disposed within bore 67 of inner catheter 61 and may be securely retained therewithin by a tubular band 69 crimped around the outside of catheter 61 against needle 31, with distal end 35 of needle 31 extending distally a short distance from distal end 65 of catheter 61.

Figure 2:
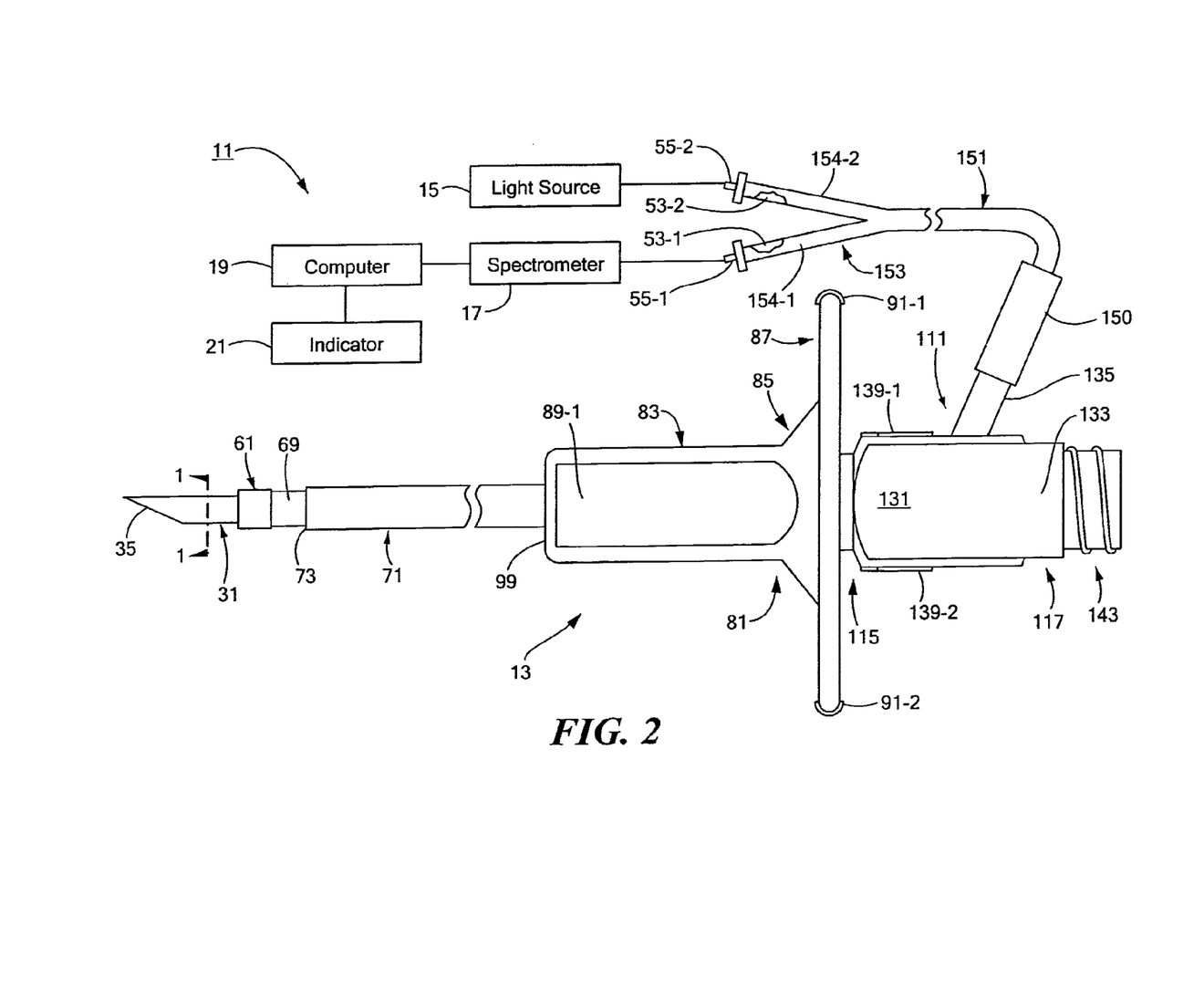
FIG. 2 illustrates a partly schematic side view, broken away in part, of the optical spectroscopic injection needle assembly of FIG. 1, the assembly being shown with its needle in an extended position.

Injection needle 13 may further comprise an outer catheter 71. In the present embodiment, outer catheter 71 may include an elongated, unitary, flexible member, for example, made of a suitable medical grade plastic, outer catheter 71 may be shaped to include a proximal end 73, a distal end 75 and a longitudinal bore 77. Outer catheter 71 may be appropriately dimensioned to receive inner catheter 61 coaxially within bore 77, with inner catheter 61 and outer catheter 71 may be slidable relative to one another. In this manner, as will be discussed further below, outer needle 31, as well as the various components housed therewithin, may be alternately extended distally from outer catheter 71, as when making an injection, and retracted into outer catheter 71, as when not making an injection.

Figure 4:
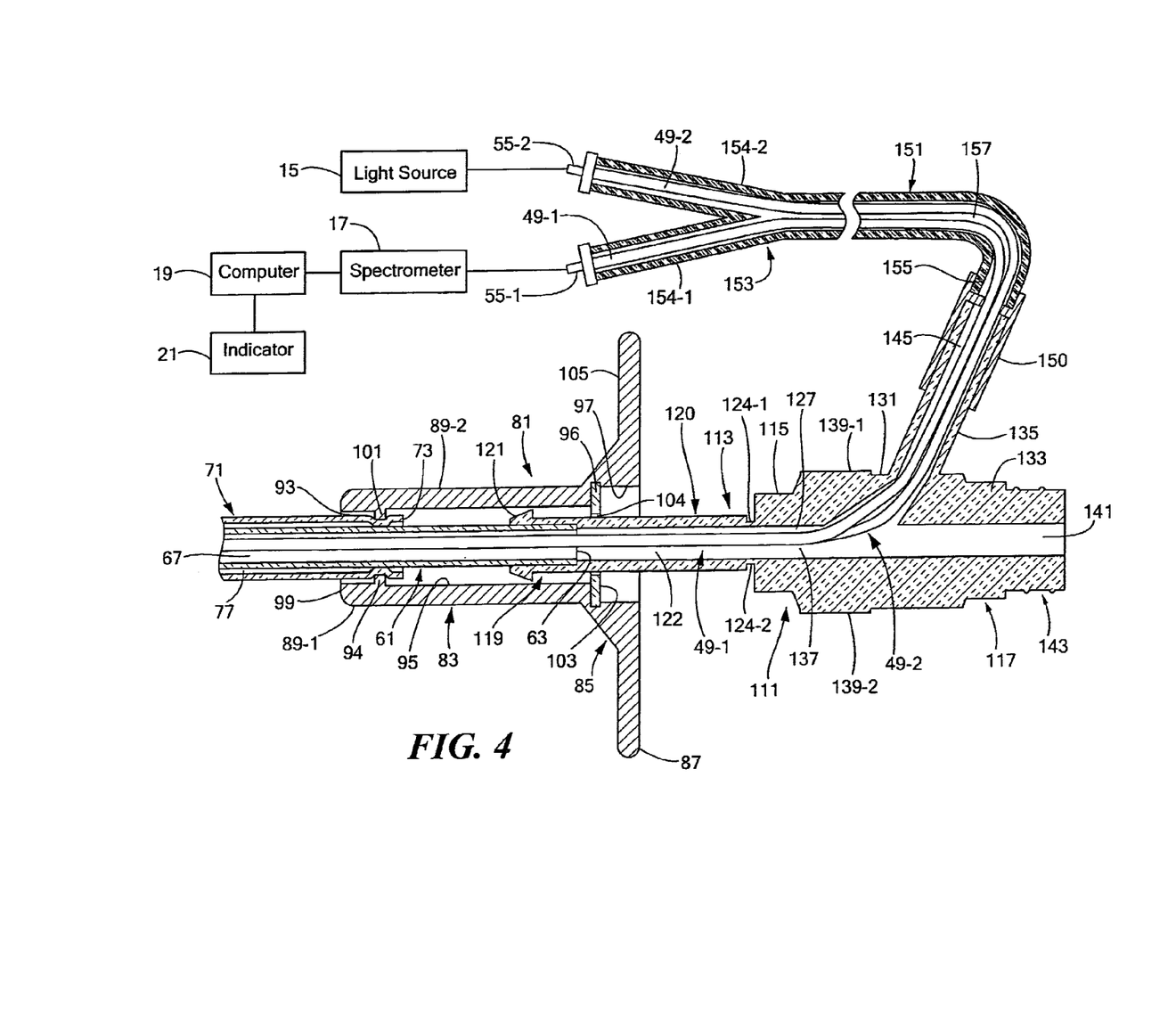
FIG. 4 illustrates a fragmentary side view, partly in section, of the proximal end of the optical spectroscopic injection needle assembly of FIG. 1.

Injection needle 13 may further comprise an outer hub 81. In one embodiment, outer hub 81 comprises an elongated, unitary, tubular, rigid member, for example, made of a suitable medical grade plastic, outer hub 81 may be shaped to include a distal stem portion 83, an intermediate shoulder portion 85, and a proximal collar portion 87. Stem portion 83 may have has an outer profile that is generally cylindrical and further may comprise a pair of opposing flattened surfaces 89-1 and 89-2 that extend longitudinally. Shoulder portion 85 may have an outer profile that is generally conical, tapering outwardly from stem portion 83 to collar portion 87. Collar portion 87, which may be generally cylindrical in outer profile, may be shaped to include embossed indicia 91-1 and 91-2, the purpose of which will be discussed further below. A longitudinal bore may be provided in outer hub 81, said longitudinal bore comprising a first portion 93, a second portion 94, a third portion 95, a fourth portion 96, and a fifth portion 97. First portion 93 may extend proximally from distal end 99 of hub 81 to second portion 94. Second portion 94, which may be smaller in diameter than first portion 93, may comprise an internal flange 101 provided in stem portion 83. Flange 101 may be appropriately dimensioned so that proximal end 73 of catheter 71, which is freely received in first portion 93, may be securely retained within outer hub 81. Outer hub 81 may be insert-molded around proximal end 73 of outer catheter 71, with internal flange 101 being sized to frictionally engage catheter 71 in a highly retentive manner. Third portion 95, which may extend between second portion 94 and fourth portion 96, may be greater in diameter than each of first portion 93 and second portion 94. Fourth portion 96, which may be located within shoulder portion 85 and which may extend between third portion 95 and fifth portion 97, may be greater in diameter than each of third portion 95 and fifth portion 97. A washer 103 may be fixedly mounted within fourth portion 97, washer 103 having a generally oval aperture 104, the purpose of which will be described below. If desired, outer hub 81 may be insert-molded around washer 103. Fifth portion 97, which may be smaller in diameter than fourth portion 96 but may be greater in diameter than third portion 95, may extend proximally from fourth portion 96 to proximal end 105 of hub 81.

Injection needle 13 may further comprise an inner hub 111. In the present embodiment, inner hub 111 may include an elongated, unitary, tubular, rigid member, for example, made of a suitable medical grade plastic, inner hub 111 being shaped to include a distal stem portion 113, an intermediate neck portion 115 and a proximal body portion 117. Stem portion 113, which may be generally cylindrical in outer profile, except for a pair of opposing flattened surfaces 118 that may extend longitudinally, may be shaped to include a slotted distal section 119 and a tubular proximal section 120. Distal section 119 may have a bifurcated barb 121 at its distal end. Proximal end 63 of inner catheter 61 may be fixedly mounted within slotted distal section 119 of stem portion 113 by a friction fit. (If desired, slotted distal section 119 may be provided with serrations to help grip inner catheter 61.) Tubular proximal section 120 may be shaped to include a longitudinal bore 122 and a pair of proximal notches 124-1 and 124-2 along its outer surface. Stem portion 113 may be partially inserted into outer hub 81, with barb 121 being appropriately sized relative to aperture 104 of washer 103 so that barb 121 may be inserted through aperture 104 during assembly of injection needle 13 but, thereafter, cannot easily be withdrawn proximally through aperture 104. In addition, tubular proximal section 120 may be dimensioned relative to aperture 104 of washer 103 so that, when stem portion 113 and aperture 104 are properly aligned rotationally, proximal section 120 may be moved back and forth through aperture 104 and so that, when stem portion 113 is fully inserted into outer hub 81 (with notches 124-1 and 124-2 disposed within aperture 104), stem portion 113 may be rotated 90 degrees relative to aperture 104, thereby preventing proximal section 120 from being moved translationally relative to outer hub 81.

Neck portion 115, which may be generally cylindrical in outer profile, may be shaped to include a longitudinal bore 127, bore 127 being aligned with bore 122 of proximal section 120. Neck portion 115 may be appropriately dimensioned to serve as a stop to limit insertion of inner hub 111 into outer hub 81.

Proximal body portion 117, which may be generally rectangular in outer profile, may be shaped to include an unbranched distal portion, i.e., a first arm 131, and a branched proximal portion, i.e., second and third arms 133 and 135, respectively. First arm 131 may be shaped to include a bore 137, bore 137 being aligned with bore 127 of neck portion 115. Embossed indicia 139-1 and 139-2 may be provided on opposing surfaces of first arm 131, indicia 139-1 and 139-2 being provided to be alignable with indicia 91-1 and 91-2, respectively, to indicate the rotational alignment of inner hub 111 to outer hub 81, such as when one wishes to prevent longitudinal movement of inner hub 111 relative to outer hub 81. Second arm 133, which is substantially coaxial with first arm 131, may be shaped to include a bore 141, bore 141 being aligned with bore 137 of first arm 131. The proximal end of second arm 133 may be shaped to include an externally threaded connector 143 adapted for use with a needle-less syringe or the like. Third arm 135, which may lie off-axis with first arm 131, may be shaped to include a bore 145, bore 145 communicating with bore 137. A flexible strain relief 150 is coaxially mounted over the free end of third arm 135.

Injection needle 13 may further comprise a sheath 151. Sheath 151 may be an elongated, unitary, flexible, tubular member, for example, a length of furcation tubing. Sheath 151 may be shaped to include a proximal end 153 and a distal end 155, proximal end 153 being bifurcated into arms 154-1 and 154-2 to hold the proximal ends of optical fibers 49-1 and 49-2, respectively. Distal end 155 of sheath 151 may be fixedly mounted within strain relief 150.

Light source 15, which may be a conventional, variable-wavelength light source (e.g., tunable laser, lamp with filters, etc.) of the type used to illuminate objects with one or more of ultraviolet, visible and infrared light for purposes of performing optical spectroscopy, may be coupled to connector 55-2 to provide light to optical fiber 49-2.

Spectrometer 17, which may be a conventional spectrometer, may be coupled to connector 55-1 to detect the light from optical fiber 49-1. Spectrometer 17 may also be electrically coupled to computer 19, which, in one embodiment, compares the detected spectrum to standards from objects whose composition is known (e.g., fat tissue, muscle tissue, blood, etc.). The results of the comparison from computer 19 may then be transmitted to indicator 21. Indicator 21 may take the form of a computer monitor, a printer, one or more light signals (e.g., a green light turned on for targeted objects, a red light turned on for other objects), one or more audio signals (e.g., a bell rung for targeted objects, a buzzer actuated for other objects), or the like.

To use assembly 11, for example, to inject implant material into the lower esophageal sphincter of a patient, one may first insert the distal end of an endoscope through the mouth of the patient and then into the esophagus of the patient in the vicinity of the lower esophageal sphincter. Placement of the distal end of the endoscope in the vicinity of the lower esophageal sphincter may be aided by real-time observation equipment loaded into a viewing channel of the endoscope. Then, one may attach a solution-containing syringe to connector 143 of injection needle 13 and may load the distal end of injection needle 13 into the working channel of the endoscope, with needle 31 being placed in a retracted position within outer catheter 71. Next, one may extend needle 31 distally from outer catheter 71 by sliding inner hub 111 into outer hub 81 until neck portion 115 of inner hub 111 abuts washer 103. One then may rotate inner hub 111 relative to outer hub 81 by 90 degrees (i.e., so that indicia 91-1 and 91-2 are aligned with indicia 139-1 and 139-2, respectively) to keep inner hub 111 and outer hub 81 from sliding relative to one another. With needle 31 thus extended distally from outer catheter 71, one may begin to insert needle 31 into a targeted area of the patient. (Visual identification of the targeted area is preferably aided by the real-time observation equipment of the endoscope.) As needle 31 is inserted into the targeted area, light from light source 15 may be transmitted to the penetrated depth of the targeted area using optical fiber 49-2. The light reflected from the illuminated area may then be collected by optical fiber 49-1, may be detected by spectrometer 17, and may be analyzed by computer 19. The results of the comparison may then be transmitted to indicator 21, which may provide an indication (e.g., visual, aural, etc.) as to whether needle 31 has been inserted into the area to an appropriate depth (e.g., to the depth at which muscle tissue is located). As can be appreciated, the aforementioned spectroscopic testing of the illuminated area may be conducted continuously so that, as one inserts needle 31 into the area to changing depths, one may obtain virtually instantaneous feedback as to whether needle 31 is positioned at the appropriate depth for the desired tissue type within the targeted area. Once an indication has been made that needle 31 has been inserted into the desired tissue type, one may dispense the solution from the syringe into the tissue using injection needle 13, the solution being conducted successively through bores 141, 137, 127, 122, 67 and 47, respectively. After the injection is complete, one may retract needle 31 into catheter 71 by rotating inner hub 111 relative to outer hub 81 by another 90 degrees (i.e., so that indicia 91-1 and 91-2 are 90 degrees out of alignment with indicia 139-1 and 139-2) and by sliding inner hub 111 proximally away from outer hub 81 until barb 121 of distal portion 113 abuts washer 103. One then may remove injection needle 13 and the endoscope from the patient.

Figure 6:
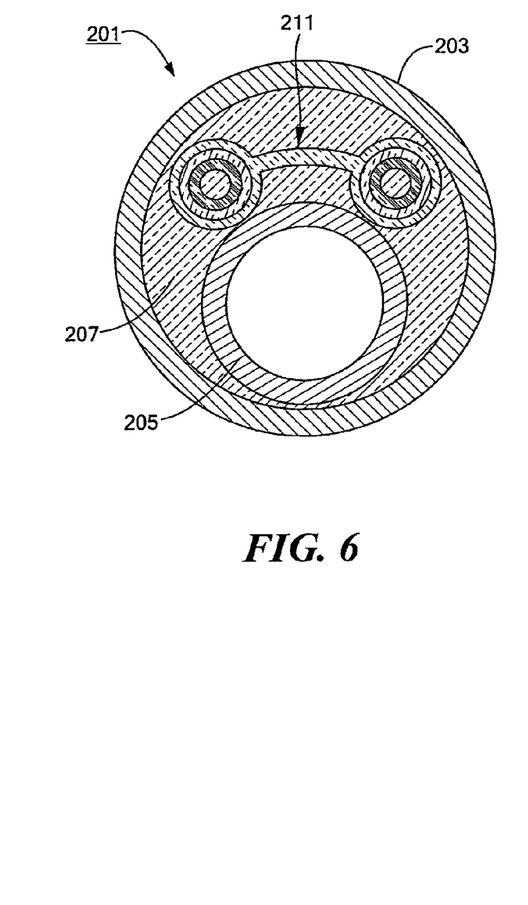
FIG. 6 illustrates an enlarged section view of an alternate needle assembly for use in the injection needle of FIG. 1.

Referring now to FIG. 6, there is shown an enlarged section view of an alternate needle assembly adapted for use in injection needle 13, said alternate needle assembly being represented generally by reference numeral 201.

Figure 7A:
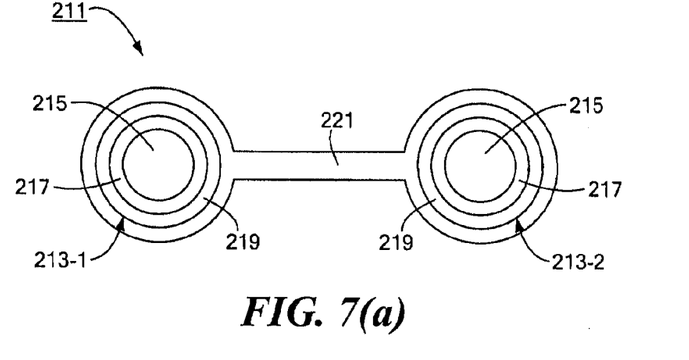
FIGS. 7(a) and 7(b) are enlarged distal end and fragmentary top views, respectively, of the fiber optic assembly illustrated in FIG. 6.
Figure 7B:
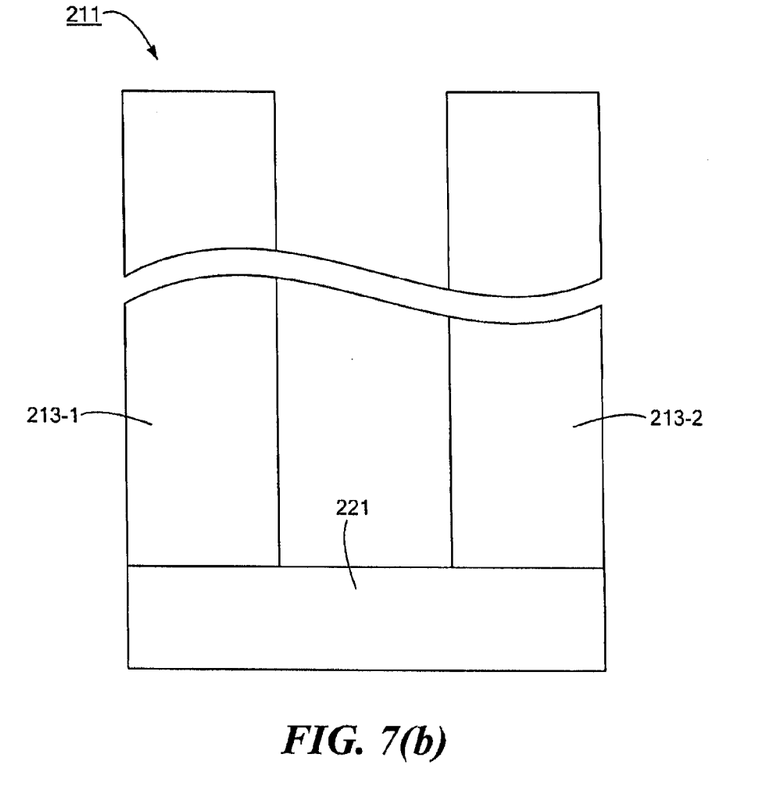

Assembly 201 is similar in many respects to the needle assembly of injection needle 13, assembly 201 including (i) an outer needle 203 that is similar to outer needle 31, (ii) an inner needle 205 that is similar to inner needle 41, and (iii) an optical bonding material 207 that is similar to optical bonding material 59. However, assembly 201 differs from the needle assembly of injection needle 13 in that, instead of including spacer 56 and optical fibers 49-1 and 49-2, assembly may include fiber optic assembly 211. Assembly 211, which is shown separately in FIGS. 7(a) and 7(b), comprises a pair of optical fibers 213-1 and 213-2. Fibers 213-1 and 213-2 may be similar in structure and composition to optical fibers 49-1 and 49-2, respectively, each of fibers 213-1 and 213-2 comprising a core 215, a cladding 217 and a buffer 219. Assembly 211 also may comprise a bundling sheath 221, bundling sheath 221 designed to coaxially surround each of fibers 213-1 and 213-2 at their respectively distal ends and physically coupling together fibers 213-1 and 213-2. In the present embodiment, sheath 221 may be made of a flexible material so that fibers 213-1 and 213-2 may assume an orientation within needle 203 similar to that assumed by fibers 49-1 and 49-2 within needle 31.

In another embodiment (not shown), the light source and/or the light detector may be positioned at or near the distal end of the injection needle. For example, an LED or other light source may be positioned at or near the distal end of the hollow needle, and a light sensor may be located on the outside of the hollow needle or integrated into the wall of the hollow needle. Alternatively, the needle itself could be an optical light guide, either to deliver light or to receive light.

It should be noted that, although the endoscopic injection needle assembly of the present invention has been described above as being used to inject implant material into LES tissue, this assembly is not limited to injecting implant materials nor is it limited to injecting materials into LES tissue. For example, it may include use as a needle to inject therapeutic and/or diagnostic agents and implants.

The embodiments of the present invention described above are intended to be merely exemplary and those skilled in the art shall be able to make numerous variations and modifications to it without departing from the spirit of the present invention. For example, it should be understood that, instead of using one optical fiber to illuminate an object and another optical fiber to collect the light reflected from the object, one could use an arrangement that includes a single optical fiber for both illumination and collection. All such variations and modifications are intended to be within the scope of the present invention as defined in the appended claims.

What is claimed is:

1. An injection needle comprising:
   (a) a first catheter, the first catheter having a proximal end, a distal end and a longitudinal bore;
   (b) a first hollow needle, the first hollow needle extending distally from the distal end of the first catheter, the first hollow needle having a sharpened beveled distal end adapted to pierce tissue; and
   (c) a tubular member, the tubular member having a longitudinal bore, the tubular member being disposed within the first hollow needle, wherein the first catheter and the tubular member are configured to allow fluid to flow from the longitudinal bore of the first catheter to the longitudinal bore of the tubular member.

2. The injection needle of claim 1, wherein the first hollow needle has a proximal end, the proximal end being fixedly mounted within the longitudinal bore of the first catheter.

3. The injection needle of claim 1, wherein each of the first catheter and the tubular member is configured to directly contact fluid flowing from the longitudinal bore of the first catheter to the longitudinal bore of the tubular member.

4. The injection needle of claim 1, wherein the first hollow needle is axially fixed relative to the tubular member.

5. The injection needle of claim 1, wherein the tubular member is a second hollow needle.

6. The injection needle of claim 5, wherein the second hollow needle has a distal-facing distal end face, the distal-facing distal end face of the second hollow needle and a distal-facing distal end face of the first hollow needle lying along a common plane.

7. The injection needle of claim 1, further comprising a bonding material disposed within the first hollow needle.

8. The injection needle of claim 7, wherein the bonding material includes epoxy.

9. The injection needle of claim 7, wherein a distal end of the bonding material includes a distal face configured to lie flush with the beveled distal end of the needle.

10. A method of treating a tissue, the method comprising the steps of:
   (a) inserting a first hollow needle into an insertion site of a body part to a first depth, the first hollow needle extending distally from the distal end of a first catheter and having a sharpened beveled distal end adapted for insertion into the body part, the first hollow needle including a tubular member disposed within a lumen of the first hollow needle, the tubular member having a longitudinal bore, wherein each of the first catheter and the tubular member is configured to directly contact and allow fluid to flow from the longitudinal bore of the first catheter to the longitudinal bore of the tubular member, the first hollow needle including fiber optics disposed within the first hollow needle and radially outward from the tubular member, for transmitting light to the body part and for collecting light reflected from the body part;
   (b) illuminating the body part at the first depth using light transmitted through the fiber optics from a light source;
   (c) detecting the light reflected from the illuminated body part at the first depth using the light detector; and
   (g) injecting a material through the tubular member and into the body part.

11. The method of claim 10, wherein the first hollow needle has a proximal end, the proximal end being fixedly mounted within the longitudinal bore of the first catheter.

12. The method of claim 10, wherein a second catheter includes a proximal end, a distal end, and a longitudinal bore, the first catheter being slidably mounted in the second catheter.

13. The method of claim 12, further including:
   extending the first needle and the first catheter relative to and distally of the second catheter.

14. The method of claim 10, further including:
   placing a syringe in fluid communication with the tubular member, wherein the syringe includes material.

15. The method of claim 10, wherein inserting a first hollow needle includes inserting a first hollow needle transorally.

16. An apparatus comprising:
   (a) a first catheter, the first catheter having a proximal end, a distal end, and a longitudinal bore;
   (b) a first hollow needle, the first hollow needle extending distally from the distal end of the first catheter, the first hollow needle having a sharpened beveled distal end adapted for penetrating tissue;
   (c) a tubular member, the tubular member having a longitudinal bore, the tubular member being disposed within the first hollow needle, wherein the first catheter and the tubular member are configured to directly contact fluid and allow fluid to flow from the longitudinal bore of the first catheter to the longitudinal bore of the tubular member; and
   (d) a second catheter, the second catheter having a proximal end, a distal end, and a longitudinal bore, the first catheter being slidably mounted in the second catheter.

17. The apparatus of claim 16, further including:
   a first hub, the first hub being coupled to the proximal end of the first catheter, the first hub comprising a connector adapted for connection to an implant source, the connector of the first hub having a bore, wherein the first catheter and the connector are configured so that fluid can flow from the bore of the connector to the longitudinal bore of the first catheter.

18. The apparatus of claim 17, further including:
a second hub, the second hub being coupled to the proximal end of the second catheter, the second hub having a bore for receiving a portion of the first hub.

19. The apparatus of claim 16, wherein the tubular member is a second hollow needle.

20. The apparatus of claim 19, wherein the second hollow needle has a distal-facing distal end face, the distal-facing distal end face of the second hollow needle and a distal-facing distal end face of the first hollow needle lying along a common plane.

* * * * *